United States Patent [19]

Chin

[11] Patent Number: 4,919,153
[45] Date of Patent: Apr. 24, 1990

[54] METHOD AND APPARATUS FOR REMOVING PRE-PLACED PROSTHETIC JOINTS AND PREPARING FOR THEIR REPLACEMENT

[75] Inventor: Albert K. Chin, Palo Alto, Calif.
[73] Assignee: Origin Medsystems, Inc., San Mateo, Calif.
[21] Appl. No.: 255,650
[22] Filed: Oct. 11, 1988
[51] Int. Cl.$^5$ ............................................. A61F 5/04
[52] U.S. Cl. ........................................ 606/93; 623/66; 606/100
[58] Field of Search ....................... 623/16, 18, 20, 22, 623/23, 66; 128/92 V, 92 VT, 92 VP, 92 VQ, 92 VJ

[56] References Cited

U.S. PATENT DOCUMENTS

| | | | |
|---|---|---|---|
| 4,222,382 | 9/1980 | Antonsson et al. | 128/92 VT |
| 4,399,813 | 8/1983 | Barber | 128/92 VT |
| 4,476,861 | 10/1984 | Dimakos et al. | 128/92 VT |
| 4,686,971 | 8/1987 | Harris et al. | 128/92 VT |
| 4,834,081 | 5/1989 | Van Zile | 128/92 VT |

*Primary Examiner*—David J. Isabella
*Attorney, Agent, or Firm*—Limbach, Limbach & Sutton

[57] ABSTRACT

A method and apparatus for removing a pre-placed prosthetic joint from a bone cavity and conditioning the cavity for receipt of a replacement joint. The pre-placed joint is first pulled from the mantle of hardened cement holding it within the cavity, thus leaving a cavity within the mantle. A mass of fluid cement is then placed within the cement cavity, after which a pulling appliance is inserted into the fluid cement and the fluid cement is permitted to cure to bond the appliance to the mantle. Tension is then applied to the pulling appliance to remove the appliance and the cement mantle from the bone cavity as a unit. The fluid cement partially dissolves and softens the hardened cement mantle so that an integral cement mass is formed upon curing of the fluid cement. The pulling appliance is of a screw-like configuration, with means to connect a slap-hammer to its proximal end.

23 Claims, 2 Drawing Sheets

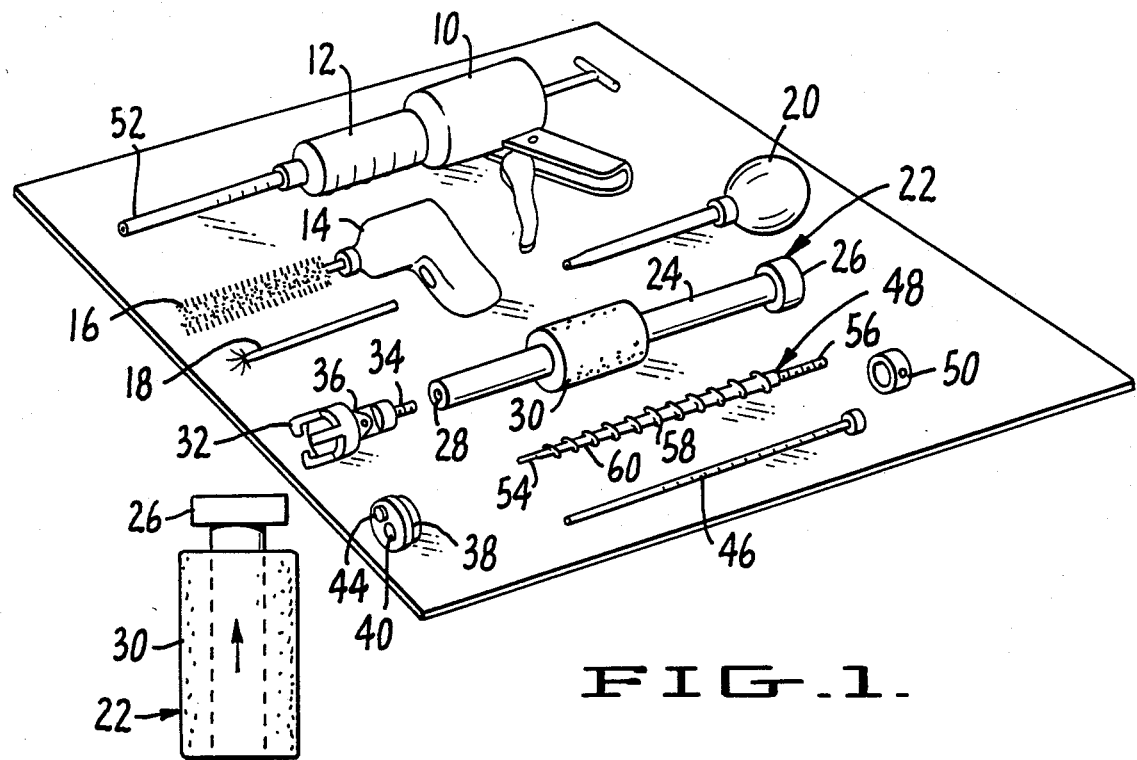
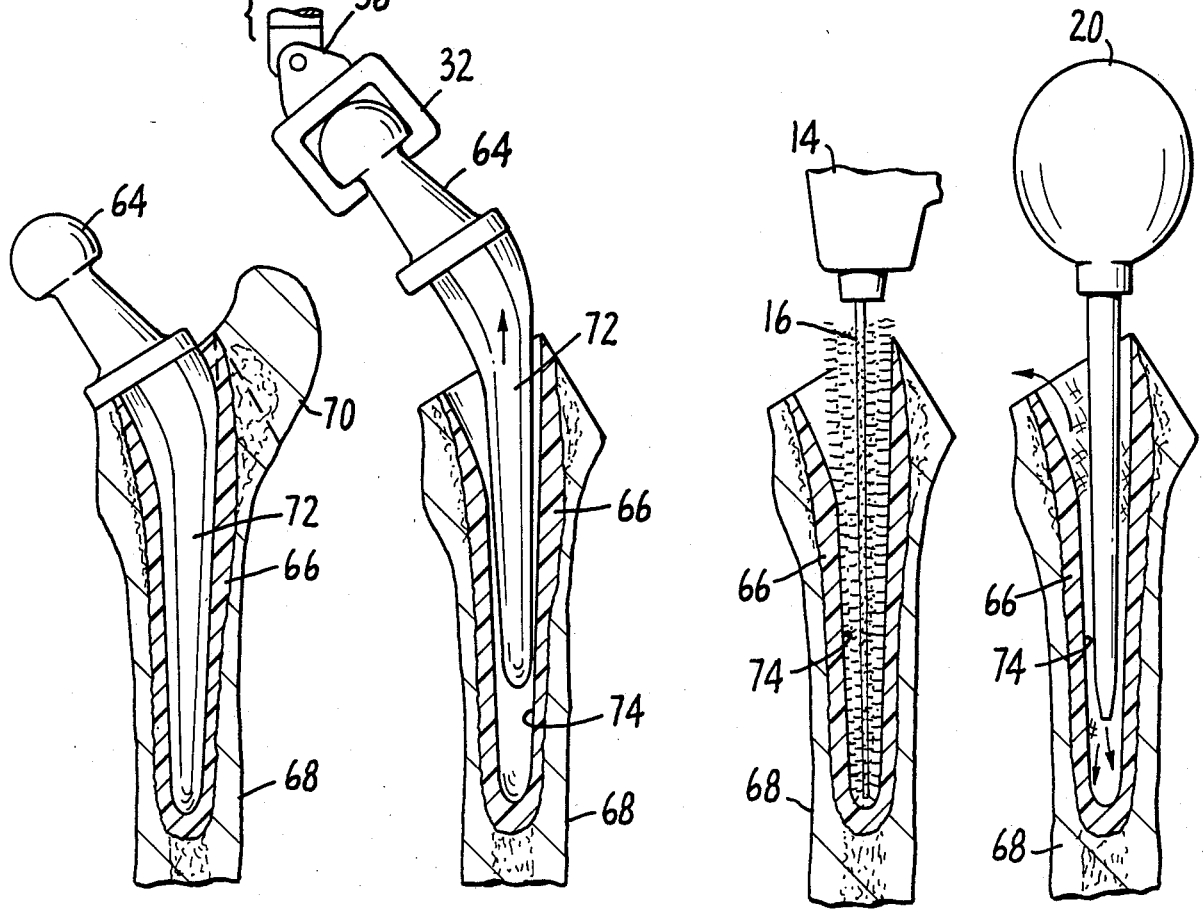
FIG.1. FIG.2 FIG.3 FIG.4 FIG.5

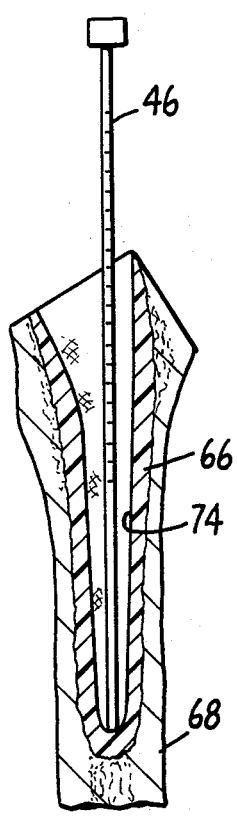
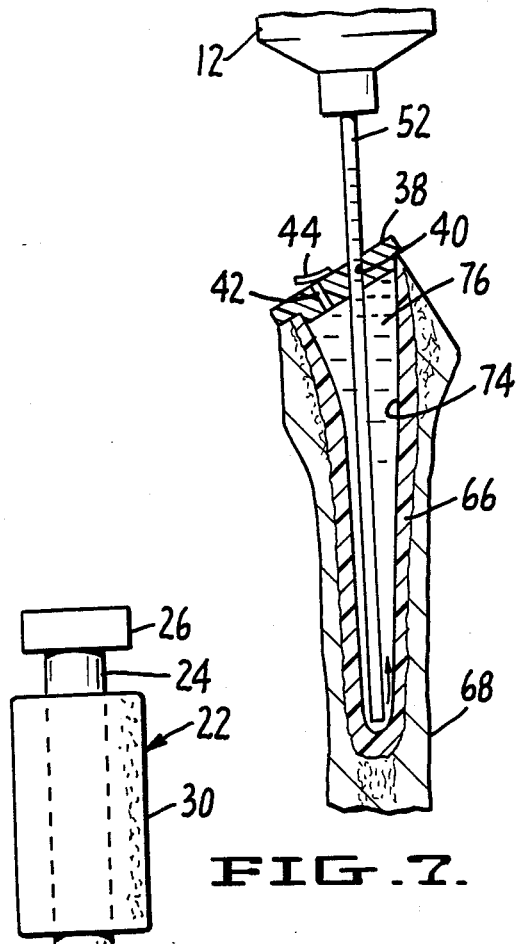
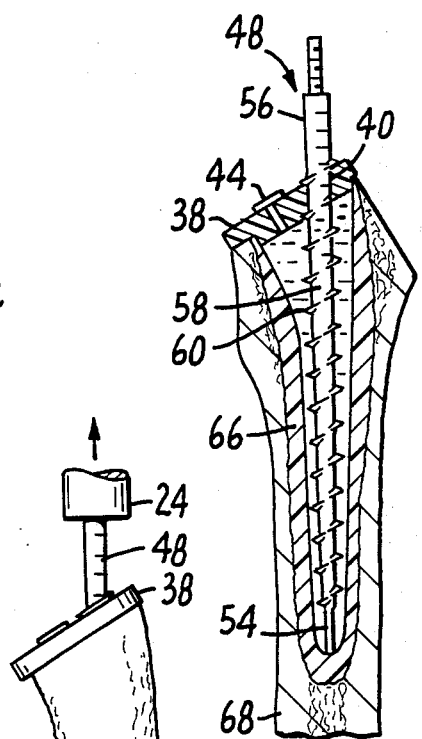
FIG. 6.   FIG. 7.   FIG. 8.
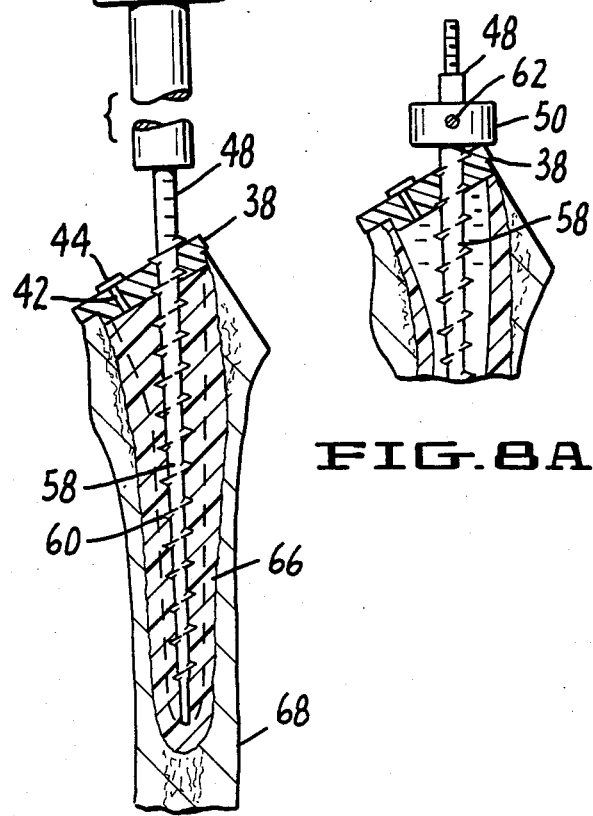
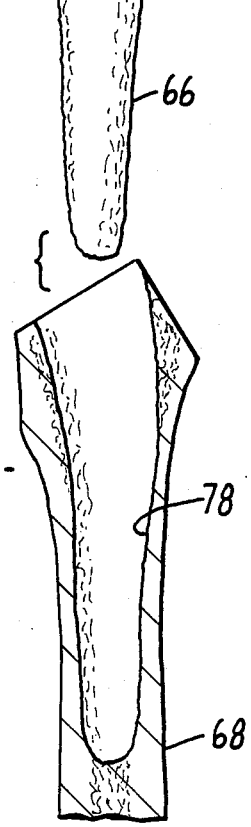
FIG. 9.   FIG. 8A.   FIG. 10.

METHOD AND APPARATUS FOR REMOVING PRE-PLACED PROSTHETIC JOINTS AND PREPARING FOR THEIR REPLACEMENT

BACKGROUND OF THE INVENTION

The present invention relates to the replacement of pre-placed prosthetic joints and, more particularly, is concerned with a method and apparatus for removing the cement mantle used to secure the pre-placed joint in place. In its more particular aspects, the invention is concerned with such a method and apparatus for removing the cement mantle to secure the ball of a prosthetic hip joint to the patient's femur.

Prosthetic hip and knee joints have become relatively commonplace. Unfortunately, however, there has also been a progressive rise in the incidence of the nonseptic failure of such joints which necessitates revision surgery to affect their replacement. The leading cause of the nonseptic failure of hip joints is the loosening of the femoral side of the prosthetic appliance. This is generally the result of loosening of the cement securing mantle for the appliance from the cavity in the femur within which the mantle is received.

Revision surgery for the replacement of a failed joint requires that both the prosthetic appliance and the mantle holding it in place within the bone cavity be removed. The old prosthetic device is usually easily removed using a slap-hammer, since its surface is smooth and separable from the underlying cement mantle. The the cement mantle, however, is tightly adherent to the surrounding bone and generally remains so adhered, even after the prosthetic device is removed. Removal of the adhered cement mantle is presently performed by progressively chipping the mantle away using a hammer and chisel. This method is tedious and the possibility of the chisel going past the mantle and fracturing the underlying bone is present. Other methods of removing the cement mantle, using powered drilling and boring devices, are similarly tedious and dangerous to the bone.

Prior revision surgery for the replacement of prosthetic hip joints also often includes a trochanteric osteotomy to remove the greater trochanter. Although this exposes the cement mantle and makes it easier to work upon, it generally does not eliminate the necessity for chipping the mantle away with a hammer and chisel to affect its removal.

SUMMARY OF THE INVENTION

Methylmethacrylate cement is the most accepted type of cement used to secure prosthetic joint appliances to bone. This cement is supplied to the surgeon packaged in two sterile components. One component is a liquid methyl methacrylate monomer and the other is a finely divided powder mixture of polymethyl methacrylate, methyl methacrylate-styrene-copolymer. At the time of use, the powder and liquid are mixed, resulting in the exothermic polymeric formation of a soft pliable dough-like mass. As the reaction progresses, with a few minutes a hard cement-like complex is formed. It is this complex which forms the cement mantle which the present invention is designed to remove.

Old hardened methylmethacrylate cement is capable of being partially dissolved and softened by the application of new like fluid cement thereto. The resulting composite of old and new cement cures into an integral bonded composite, generally within about ten minutes. Although the present invention relies upon this characteristic of methylmethacrylate cement, it may find equal application to other cements, so long as an adequate bond is provided between the old and new cement.

In the method of the present invention, a mass of new fluid methylmethacrylate cement is placed in intimate contact with the hardened mantle of old methylmethacrylate cement desired to be removed. A pulling appliance is then imbedded within the fluid cement and the mass of cement is permitted to cure and harden, thus forming a bond between the appliance and the mantle of old cement. Tension is then applied to the pulling mantle to pull the appliance and bonded mantle from the bone.

The pulling appliance of the invention comprises a rigid post of generally rectilinear configuration having an irregular outer surface. The irregular outer surface is formed by an elongated tapered section on the post which converges towards its distal end. A helical screw thread is formed around and extends over the length of the tapered section. The proximal end of the post is provided with means to secure a slap-hammer thereto.

The unobviousness of the present invention becomes particularly apparent when it is appreciated that the concept of adding cement to a mantle desired to be removed is abhorrent to normal removal practice. The normal practice is only to remove material, as for example by chipping it away. The thought of adding new material naturally engenders the concern that it will aggravate the situation by increasing the mass of material which must be removed and making it less accessible to conventional removal instruments.

A principle object of the present invention is to provide an improved method and apparatus for removing a cement mantle from adhered condition within a bone cavity.

Another object of the invention is to provide such a method and apparatus which enables the mantle to be removed intact, as a unit.

Still another object of the invention is to provide such a method and apparatus which avoids the necessity of chipping away at the mantle to effect its removal.

Another and more general object of the invention is to provide such a method and apparatus which enables the removal of the mantle quickly and efficiently, with a minimum of trauma to the patient being treated.

A further general object of the invention is to provide such a method and apparatus which minimizes the risk of damage to the bone from which the mantle is being removed.

These and other objects will become more apparent from the following detailed description and accompanying drawings.

BRIEF DESCRIPTION OF THE DRAWING

FIG. 1 is a perspective view illustrating the kit of equipment used to practice the method of the invention, including the pulling post;

FIG. 2 is a cross-sectional elevational view of the upper femur of a leg with the femoral component of a prosthetic hip joint secured therein, and a dashed line showing the step of removing the greater trochanter from the femur;

FIG. 3 is a cross-sectional elevational view similar to FIG. 2, illustrating the step of removing the femoral component of the prosthetic hip joint from the cement mantle within the femur;

FIG. 4 is a cross-sectional elevational view similar to FIG. 3, illustrating the step of using a rotary brush to abrade the cavity left in the cement mantle by removal of the femoral component of the hip joint;

FIG. 5 is a cross-sectional elevational view similar to FIG. 4, illustrating the step of irrigating the cavity within the cement mantle;

FIG. 6 is a cross-sectional elevational view similar to FIG. 5, illustrating the step of measuring the cavity of the cement mantle;

FIG. 7 is a cross-sectional elevational view similar to FIG. 6, illustrating the step of filling the cavity in the cement mantle with fluid cement;

FIG. 8 is a cross-sectional elevational view similar to FIG. 7, illustrating the step of placing the pulling tool within the fluid cement;

FIG. 8A is a cross-sectional elevational view similar to FIG. 8, with parts thereof broken away, illustrating the stop which may be used to limit the degree to which the pulling tool is extended into the cavity in the cement mantle;

FIG. 9 is a cross-sectional elevational view similar to FIG. 8, illustrating the step of using a slap-hammer to apply tension to the cement mantle through the pulling tool; and, FIG. 10 is a cross-sectional elevational view similar to FIG. 9, illustrating the step of removing the cement mantle from the femur, as a unit.

DESCRIPTION OF THE PREFERRED EMBODIMENTS

The kit shown in FIG. 1 includes the following components: injection gun 10 having a cement cartridge 12 secured thereto; rotary drill 14 having a longitudinally extending circumferential brush 16 secured in the chuck thereof; distal brush 18 adapted to be secured to the chuck of the drill 14 in place of the brush 16; irrigation syringe 20; slap-hammer 22 having a cylindrical shaft 24 with a stop 26 on the distal end thereof, a screw threaded socket 28 in the proximal end thereof, and an annular weight 30 slidably received thereon for abutting engagement with the stop 26; a ball clamp 32 having a screw threaded shaft 34 secured therego by an articulated joint 36, said shaft being designed for threaded engagement in the socket 28 of the slap-hammer 22; a cement restrictor plug 38 fabricated of an elastomeric material and having an injector passage 40 and a vent passage 42 (see FIG. 7) extending therethrough, said vent passage having a flap valve 44 thereover; a depth gauge 46; a pulling appliance 48; and, a stop collar 50.

Except for the pulling appliance 48 and the stop collar 50, all of the instruments in the kit are conventional. The pulling appliance and collar are especially designed for use in the method of the present invention. While the cement cartridge 12 is conventional, it is especially chosen to have a narrow snout 52 for insertion into the cavity of the cement mantle intended to be removed.

The pulling appliance 48 has a length and cross section sufficient to enable it to be extended to the bottom of the cavity in the mantle in which it is intended to be used, without imparting lateral forces to the wall of the cavity. Ideally, its outside diameter closely mimics, but is slightly less than that of the femoral component which formed the cavity. The appliance may be fabricated of any suitable high tensile strength corrosion-resistant material, such as stainless steel.

The pulling appliance provides a rigid post of generally rectilinear configuration having a distal end 54 and a proximal end 56. An elongated tapered section 58 is formed on the post between its proximal and distal ends and has a helical screw thread 60 formed therearound. As may be seen from FIGS. 8 and 9, both the section 38 and thread 60 taper so as to converge toward the distal end 54 of the post. The proximal end 56 provides a screw threaded shaft for receipt in the socket 28 of the slap-hammer 22. The distal end 54 is axially aligned with the proximal end 56 and of a cylindrical reduced diameter cross-section, as compared to that of the tapered section 58. As can be seen from FIGS. 8 and 9, the distal end serves as a stop to limit the degree to which the pulling instrument may penetrate the cavity in the cement mantle. Its reduced cross-section assures that space is provided therearound for receipt of fluid cement, as will become more apparent from the following description of the method.

The stop collar 50 is proportioned for slidable receipt over the pulling appliance 48 and is provided with a set screw 62 extensible therethrough into engagement with the post of the appliance. Thus, the collar may be slid along the length of the appliance and locked thereto at any desired position.

FIGS. 2 through 10 sequentially illustrate the steps of the method in removing the femoral component 64 of a hip joint and the cement mantle 66 therefor from the femur 68. It should be appreciated that as shown in FIG. 2 femoral component 64 has been secured to the femur 68 through the cement mantle 66 in conventional manner. The problem to be solved by the present invention is the removal of the component and mantle so that the joint can be renewed.

FIG. 2 shows the preparatory step of removing the torchantere 70 of the femur. The dashed line in FIG. 2 designates the saw line for the trochanteric osteotomy used to remove the trochanter. This line is chosen so as to intersect the mantle 66, while at the same time leaving a sufficient bone interface so that the trochanter may be reattached to the femur. So removing the trochanter increases access to the mantle 66 and aids in assuring that pulling of the mantle from the femur will not damage the bone structure.

FIG. 3 shows the step of pulling the femoral component 64 from the mantle 66. For this purpose, the ball lamp 32 is secured to the component and the slap-hammer 22 is attached to the clamp through means of the articulated joint 36. Once the clamp and hammer are so connected, the position of the hammer is adjusted so that is axis is generally parallel to the axis of the femoral component extension, designated 72. The weight 30 is then slid along the slap hammer to impact with the stop 26, thus applying impact tension to the femoral component and pulling it from the mantle 66, as indicated by the arrow lines in FIG. 3. Removal of the femoral component from the mantle leaves a cement cavity, designated 72 therein.

FIGS. 4 and 5 show the steps of abrading and cleaning the interior of the cavity 74. As shown in FIG. 4, the cavity is being circumferentially brushed by the brush 16 connected to the drill 14. FIG. 5 shows the cavity being irrigated by the syringe 20. Although not illustrated, it should be appreciated that the distal end of the cavity may be additionally brushed by attaching the distal brush 18 to the drill 14 and extending the brush to the bottom of the cavity. After irrigation, the cavity may be dried by swabbing or blowing.

FIG. 6 shows the step of using the gauge 46 to measure the depth of the cavity 74. The depth measurement thus achieved is transposed to the pulling appliance 48 so that it may serve as a guide to limit the degree to which the appliance is later inserted into the cavity. This transposition may be by either marking the pulling instrument to indicate the measurement, or securing the stop collar 50 to the instrument by means of the set screw 62 (see FIG. 8A). Regardless of how the transposition is achieved, the purpose is the same, namely to assure that the pulling instrument will not be forced into the bottom of the mantle 66.

FIG. 7 shows the step of placing the plug 38 in the open proximal end of the mantle 66 and injecting fluid cement into the cavity 74 by means of the snout 52. The mass of fluid cement so injected into the cavity is designated by the numeral 76. In the preferred embodiment, the fluid cement corresponds to that from which the mantle was originally fabricated and functions to soften and partially dissolve the mantle. For example, if methylmethachrylate cement is used for both the mantle and the fluid mass, such dissolution and softening will occur. As the fluid cement is injected into the cavity 74, air is vented through the vent hole 42. Upon filling of the cavity, continued injection of cement functions to apply upward pressure to the snout 52 and the snout is slowly withdrawn, thus forming a void-free mass of cement within the cavity.

FIG. 8 shows the step of inserting the pulling appliance 48 into the cement mass 76 while the mass is still in a fluid state. This is achieved by screwing the threads of the instrument through the passage 40 and into the mass to the point where the distal end 54 engages the bottom of the cavity 74. The point of such engagement may be determined both by feel and by the previous measurement transposed to the pulling appliance from the depth gauge 46. The screwing of the appliance 48 into the fluid mass of cement is carried out in a relatively slow controlled fashion so as to avoid the creation of voids within the mass. This poses no particular problem, since it takes approximately ten minutes for the mass to cure to a hardened state.

FIG. 9 shows the mass of cement 66 after is has cured to a hardened integral state with the mantle 66 and bonded to the pulling appliance 48. As there shown, the slap-hammer is threadably secured to the proximal end of the appliance.

FIG. 10 shows the final step wherein the slap hammer 22 is used to apply impact tension to the pulling instrument 22, thus pulling the instrument and the mantle bonded thereto from the femur, as a unit. This step leaves the original bone cavity, designated 78, within the femur in a clean state. Thereafter, a new prosthetic joint may be cemented into the bone cavity.

CONCLUSION

While a preferred embodiment of the invention has been illustrated and described, it should be understood that the invention is not limited to this embodiment. For example, it is anticipated that the invention may find use in the removal of a cement mantle in other than a joint replacement application and that it may be used in replacing joints other than hip joints.

I claim:

1. A method for removing a prosthetic appliance secured in place by a mantle of hardened methylmethacrylate cement received within a bone cavity and conditioning the bone cavity for receipt of a new appliance, said method comprising:
   (a) pulling the appliance from the mantle of hardened cement to leave a cement cavity within the mantle;
   (b) injecting a fluid mass of methylmethacrylate cement into the cement cavity;
   (c) inserting a post having an irregular exterior surface into the fluid mass of methtylemethacrylate cement;
   (d) permitting said fluid mass of methylemethacrylate cement to harden and bond to the post and the hardened mantle; and,
   (e) applying tension to the post to pull the post and the bonded mantle of methylemethacrylate cement from the bone cavity.

2. A method according to claim 1 further comprising abrading and cleaning the cement cavity prior to injecting the fluid mass of methylemethacrylate cement into said cavity.

3. A method according to claim 2 further comprising:
   (a) measuring the depth of the cement cavity prior to inserting the post into the mass of fluid cement; and,
   (b) controlling the depth to which the post is inserted into the cement cavity so that the penetration of the post into the cement cavity does not exceed the depth thereof.

4. A method according to claim 1 wherein the step of injecting the fluid mass of cement into the cement cavity comprises:
   (a) placing a cap over the open end of the cement cavity;
   (b) extending a nozzle through the cap to the bottom of the cement cavity;
   (c) forcing fluid cement into the bottom of the cement cavity through the nozzle while venting air from the top of the cement cavity until the cavity is substantially full of said fluid cement; and,
   (d) withdrawing the nozzle from the cement cavity while continuing to force fluid cement through the nozzle to fill the cement cavity with a void free mass of fluid cement.

5. A method according to claim 4 wherein the post is inserted into the fluid mass of cement through the cap.

6. A method according to claim 1 wherein:
   (a) the post is generally rectilinear and the irregular surface thereof comprises helical threads; and,
   (b) the post is inserted into the mass of fluid cement by turning the post about its longitudinal axis to screw the threads into the fluid cement.

7. A method according to claim 6 wherein:
   (a) the post has a distal end and a tapered section which converges toward a distal end;
   (b) the threads are formed on the tapered section; and,
   (c) the post is screwed into the fluid cement distal end first.

8. A method according to claim 7 wherein the distal end of the post comprises a section of reduced diameter extending from the tapered section.

9. A method according to claim 1 wherein tension is applied to the post by securing a slap-hammer to the post and subjecting the post to impact tension through the slap-hammer.

10. A method according to claim 9 wherein the post is rectilinear and the impact tension is applied in generally axial alignment relative thereto.

11. A method for removing a hardened mantle of methylemethacrylate cement adhered to a bone, said method comprising:
   (a) placing a mass of fluid methylemethacrylate cement in intimate contact with the hardened mantle of cement to at least partially dissolve and soften the hardened mantle;
   (b) imbedding a pulling appliance within the fluid cement;
   (c) permitting the fluid mantle of cement and softened mantle to cure and bond together; and,
   (d) applying tension to the pulling appliance to pull the appliance and the bonded mantle from the bone.

12. A method according to claim 11, wherein:
   (a) a cavity is formed in the hardened mantle prior to placing the fluid mass of cement;
   (b) the fluid mass of cement is placed within the cavity formed in the mantle; and,
   (c) the pulling appliance is imbedded in the fluid mass of cement so as to extent into the cavity formed in the mantle.

13. A method for removing a pre-placed prosthetic hip joint secured in place within a bone cavity in the end of the femur adjacent the torchanter by a mantle of hardened cement and conditioning the bone cavity for receipt of a new joint, said method comprising:
   (a) pulling the pre-placed joint from the mantle of hardened cement to leave a cement cavity within the mantle;
   (b) injecting a mass of fluid cement into the cement cavity;
   (c) inserting a post having an irregular exterior surface into the mass of fluid cement;
   (d) permitting said mass of fluid cement to harden and bond to the post and the hardened mantle; and,
   (e) applying tension to the post to pull the post and the bonded mantle of cement from the bone cavity.

14. A method according to claim 13 further comprising cutting the trochanter off of the femur to expose the hardened mantle within the bone cavity prior to pulling the pre-placed joint from the mantle.

15. A method according to claim 13 further comprising abrading and cleaning the cement cavity prior to injecting the mass of fluid cement into said cavity.

16. A method according to claim 15 further comprising:
   (a) measuring the depth of the cement cavity prior to inserting the post into the mass of fluid cement; and,
   (b) controlling the depth to which the post is inserted into the cement cavity so that the penetration of the post into the cement cavity does not exceed the depth thereof.

17. A method according to claim 13 wherein the step of injecting the mass of fluid cement into the cement cavity comprises:
   (a) placing a cap over the open end of the cement cavity;
   (b) extending a nozzle through the cap to the bottom of the cement cavity;
   (c) forcing fluid cement into the bottom of the cement cavity through the nozzle while venting air from the top of the cement cavity until the cavity is substantially full of said fluid cement; and,
   (d) withdrawing the nozzle from the cement cavity while continuing to force fluid cement through the nozzle to fill the cement cavity with a void free mass of fluid cement.

18. A method according to claim 17 wherein the post is inserted into the mass of fluid cement through the cap.

19. A method according to claim 13 wherein:
   (a) the post is generally rectilinear and the irregular exterior surface thereof comprises helical threads; and,
   (b) the post is inserted into the mass of fluid cement by turning the post about its longitudinal axis to screw the threads into the fluid cement.

20. A method according to claim 19 wherein:
   (a) the post has a distal end and a tapered section which converges toward distal end;
   (b) the threads are formed on the tapered section; and,
   (c) the post is screwed into the fluid cement distal end first.

21. A method according to claim 20 wherein the distal end of the post comprises a section of reduced diameter extending from the tapered section.

22. A method according to claim 13 wherein tension is applied to the post by securing a slap-hammer to the post and subjecting the post to impact tension through the slap-hammer.

23. A method according to claim 22 wherein the post is rectilinear and the impact tension is applied in generally axial alignment relative thereto.

* * * * *